(12) United States Patent
Wollenweber et al.

(10) Patent No.: US 8,532,357 B2
(45) Date of Patent: Sep. 10, 2013

(54) METHOD AND APPARATUS FOR REDUCING IMAGE ARTIFACTS

(75) Inventors: Scott David Wollenweber, Waukesha, WI (US); Kris Filip Johan Jules Thielemans, Putney (GB)

(73) Assignee: General Electric Company, Schenectady, NY (US)

( * ) Notice: Subject to any disclaimer, the term of this patent is extended or adjusted under 35 U.S.C. 154(b) by 1152 days.

(21) Appl. No.: 12/358,829

(22) Filed: Jan. 23, 2009

(65) Prior Publication Data
US 2010/0189324 A1    Jul. 29, 2010

(51) Int. Cl.
*G06K 9/00* (2006.01)
(52) U.S. Cl.
USPC ............................ 382/131; 382/107; 382/275
(58) Field of Classification Search
USPC ......................... 382/107, 131, 275; 600/407
See application file for complete search history.

(56) References Cited

U.S. PATENT DOCUMENTS

| | | | |
|---|---|---|---|
| 7,397,035 B2 | 7/2008 | Watson | |
| 2005/0123183 A1* | 6/2005 | Schleyer et al. | 382/131 |
| 2008/0224050 A1 | 9/2008 | Thielemans et al. | |
| 2008/0226149 A1* | 9/2008 | Wischmann et al. | 382/131 |

OTHER PUBLICATIONS

Mohammad Dawood et al.; "Respiratory Gating in Positron Emission Tomography: A Quantitative Comparison of Different Gating Schemes"; Med. Phys.37(7),Jul. 2007; pp. 3067-3076.
Daniel A. Low et al.; "A Method for the Reconstruction of Four-Dimensional Synchronized CT Scans Acquired During Free Breathing"; Med. Phys. 30 (6), Jun. 2003; pp. 1254-1263.
Wei Lu et al.; "A Comparison Between Amplitude sorting and Phase-Angle Sorting Using External Respiratory Measurement for 4D CT"; med. Phys. 33 (8) Aug. 2006; pp. 2964-2974.

* cited by examiner

*Primary Examiner* — Arnold Kinkead
*Assistant Examiner* — Richard Tan
(74) *Attorney, Agent, or Firm* — The Small Patent Law Group; Dean D. Small

(57) ABSTRACT

A method and apparatus are provided for reducing motion related imaging artifacts. The method includes obtaining an image data set of a region of interest in an object, obtaining a motion signal indicative of motion of the region of interest, and determining a displacement and a phase of at least a portion of the motion signal. The method also includes mapping the image data set into a matrix based on the displacement and phase of the motion signal, and generating an image of the region of interest from the matrix.

13 Claims, 5 Drawing Sheets

METHOD AND APPARATUS FOR REDUCING IMAGE ARTIFACTS

BACKGROUND OF THE INVENTION

The invention relates generally to imaging systems, and more particularly, embodiments relate to an apparatus and method for reducing image artifacts that are produced by movement of an object.

Multi-modality imaging systems exist that scan using different modalities, such as, for example, Computed Tomography (CT), Magnetic Resonance Imaging (MRI), Positron Emission Tomography (PET), and Single Photon Emission Computed Tomography (SPECT). During operation, conventional imaging systems may exhibit image quality that is affected by motion of the object being imaged.

Motion of the object being imaged may degrade image quality, for example in medical imaging. More specifically, image artifacts are produced by movement of the object. Respiratory motion is a common source of involuntary motion in mammals (e.g., people and animals) encountered in medical imaging systems. The respiratory motion may lead to errors, such as when a physician is determining the size of a lesion, determining the location of the lesion, or quantifying the lesion.

To correct for motion related imaging artifacts, at least one conventional imaging system utilizes respiratory information. In cases where the data acquisition period is relatively long, conventional imaging systems monitor the patients' breathing using a respiration monitor. The signal generated by the respiration monitor is then used to reduce artifacts in the acquired image data. The conventional motion correction method relies on the assumption that the movement of internal structures in a region of interest is the same over different breathing cycles. However, involuntary motion during respiration may cause a hysteresis effect to occur.

Conventional imaging systems ignore the hysteresis effect resulting in increased motion related artifacts. The hysteresis effect occurs when the movement path followed by the internal structure during inspiration does not coincide with the path followed by the internal structure during expiration. Also, in some cases, the movement of the internal structure may lag behind the respiration signal. For example, deep breathing may cause the internal structure to be at a different position than when shallow breathing is performed. Moreover, if the object breathes faster or slower, the movement of some internal structures may exhibit a delay in reacting to the changes in direction of diaphragm movement.

BRIEF DESCRIPTION OF THE INVENTION

In one embodiment, a method for reducing, in an images motion related imaging artifacts is provided. The method includes obtaining an image data set of a region of interest in an object, obtaining a motion signal indicative of motion of the region of interest, and determining a displacement and a phase of at least a portion of the motion signal. The method also includes mapping the image data set into a matrix based on the displacement and phase of the motion signal, and generating an image of the region of interest from the matrix.

In another embodiment, a multi-modality imaging system is provided. The multi-modality imaging system includes a first modality unit, a second modality unit, and a computer operationally coupled to the first and second modality units. The computer is programmed to obtain an image data set of a region of interest in an object, obtain a motion signal indicative of motion of the region of interest, determine a displacement and a phase of at least a portion of the motion signal, gate the image data set into a matrix based on the displacement and phase of the motion signal, and generate an image of the region of interest from the matrix.

In a further embodiment, a computer readable medium is provided. The computer readable medium is programmed to instruct a computer to obtain an image data set of a region of interest in an object, obtain a motion signal indicative of motion of the region of interest, determine a displacement and a phase of at least a portion of the motion signal, gate the image data set into a matrix based on the displacement and phase of the motion signal, and generate an image of the region of interest from the matrix.

DETAILED DESCRIPTION OF THE INVENTION

Figure 1:
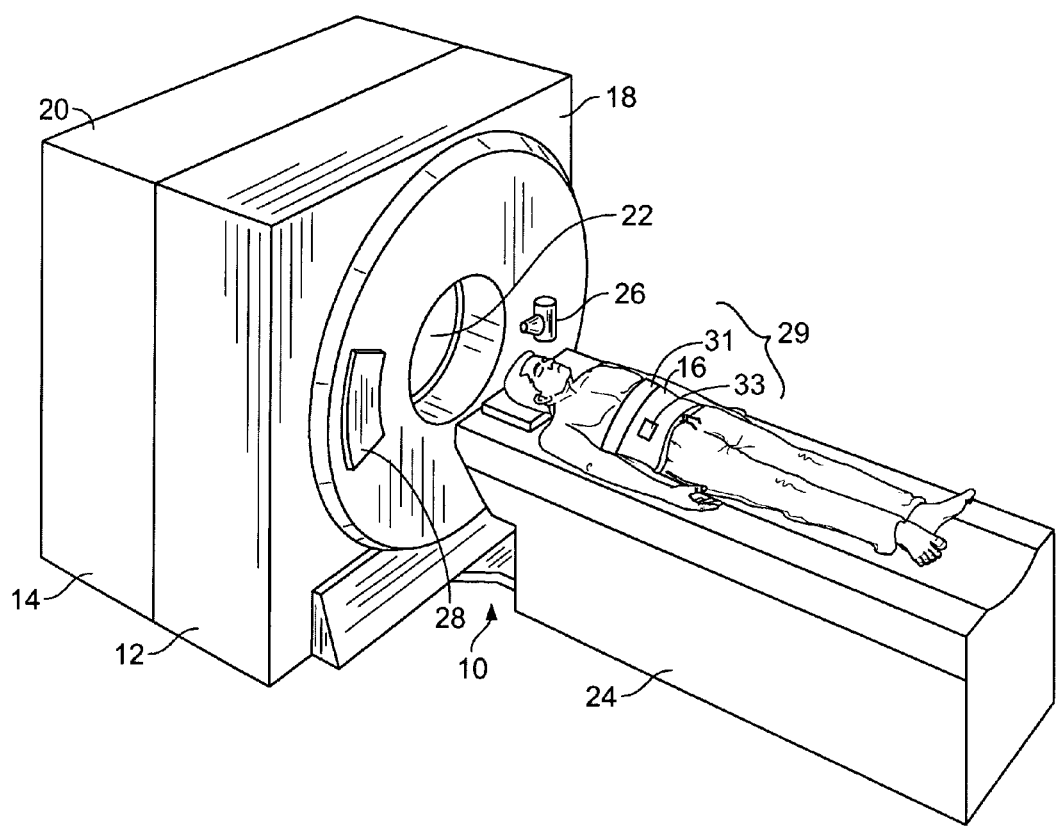
FIG. 1 is a pictorial view of an exemplary multi-modality imaging system in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 2:
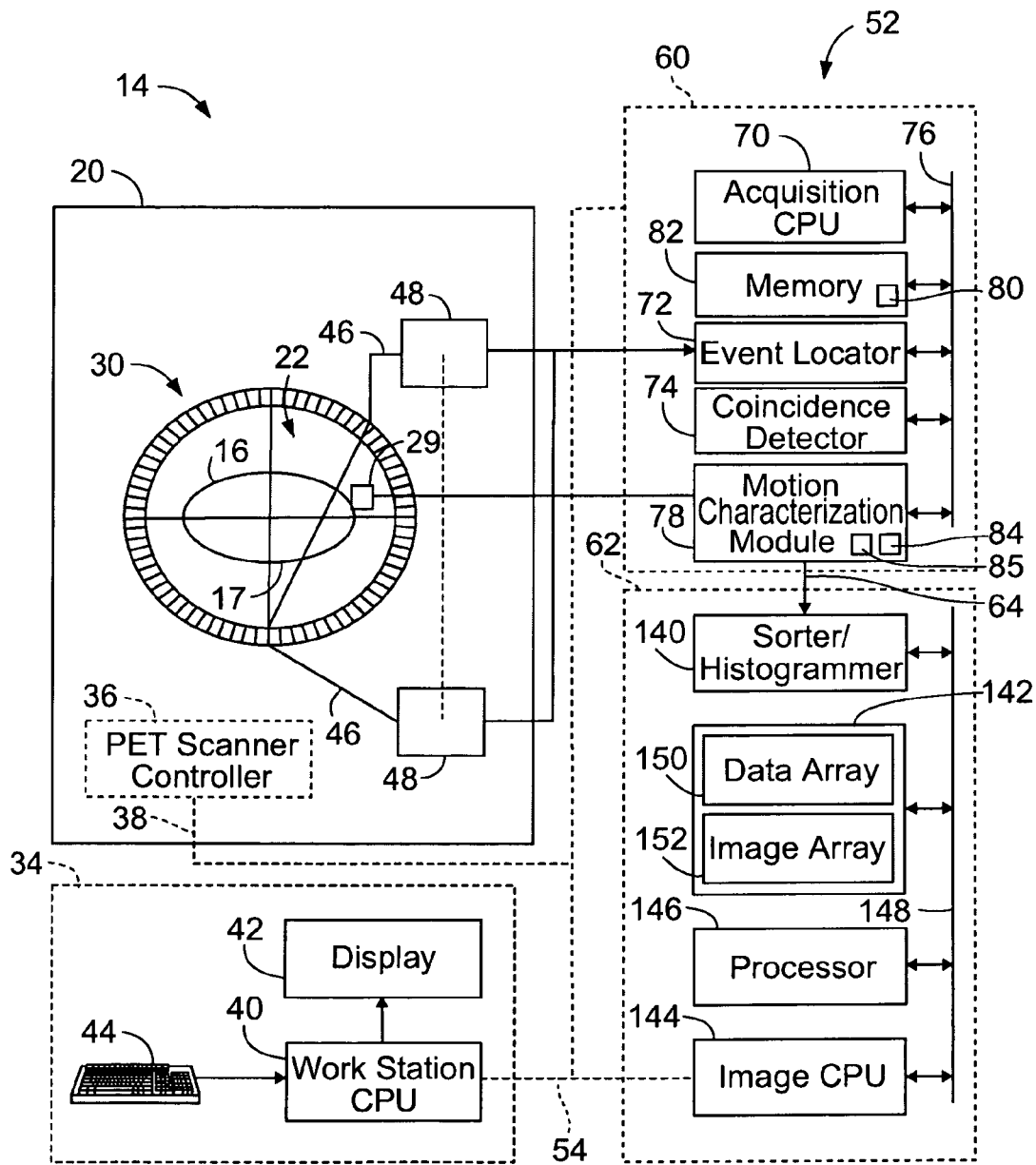
FIG. 2 is a block schematic diagram of the system illustrated in FIG. 1 in accordance with an embodiment of the present invention.

Various embodiments of the invention provide a multi-modality imaging system 10 as shown in FIGS. 1 and 2. Multi-modality imaging system 10 may be any type imaging system, for example, different types of medical imaging systems, such as a Positron Emission Tomography (PET), a Single Photon Emission Computed Tomography (SPECT), a Computed Tomography (CT), an ultrasound system, Magnetic Resonance Imaging (MRI) or any other system capable or generating tomographic images. The various embodiments are not limited to multi-modality medical imaging systems, but may be used on a single modality medical imaging system such as a stand-alone PET imaging system or a stand-alone SPECT imaging system, for example. Moreover, the various embodiments are not limited to medical imaging systems for imaging human subjects, but may include veterinary or non-medical systems for imaging non-human objects etc.

Referring to FIG. 1, the multi-modality imaging system 10 includes a first modality unit 12 and a second modality unit 14. The two modality units enable the multi-modality imaging system 10 to scan an object or patient 16 in a first modality using the first modality unit 12 and to scan the object 16 in a second modality using the second modality unit 14. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10, e.g. the first modality 12 is a CT imaging system and the second modality 14 is a PET imaging system. The CT/PET system 10 is shown as including a gantry 18 that is associated with a CT imaging system and a gantry 20 that is associated with a PET imaging system. During operation, the object 16 is positioned within a central opening 22, defined through the imaging system 10, using, for example, a motorized table 24.

The gantry 18 includes an x-ray source 26 that projects a beam of x-rays toward a detector array 28 on the opposite side of the gantry 18. Detector array 28 is formed by a plurality of detector rows (not shown) including a plurality of detector elements which together sense the projected x-rays that pass through the object 16. Each detector element produces an electrical signal that represents the intensity of an impinging x-ray beam and hence allows estimation of the attenuation of the beam as it passes through the object 16. During a scan to acquire x-ray projection data, gantry 18 and the components mounted thereon rotate about a center of rotation.

The imaging system 10 also includes at least one motion sensor 29 that is adapted to detect and transmit information that is indicative of the motion of the object 16. In one embodiment, the motion sensor 29 may be a belt-type motion sensor 31 that is adapted to extend at least partially around the object 16. Optionally, the motion sensor 29 may be a motion sensor 33 that is adapted to be secured to a predetermined position on the object 16. It should be realized that although two different motion sensors or detectors are illustrated, that the imaging system may include other types of motions sensors to generate motion related information.

FIG. 2 is a block schematic diagram of the PET imaging system 14 illustrated in FIG. 1 in accordance with an embodiment of the present invention. The PET imaging system 14 includes a detector ring assembly 30 including a plurality of detector scintillators. Each scintillator may be coupled by a light guide to multiple photomultiplier tubes (PMTs) or other light sensors that convert the light from the scintillator assembly into an electric signal. In addition to the scintillator-PMT combination, pixilated solid-state direct conversion detectors (e.g., CZT) may also be used to generate electric signals from the impact of the photons.

The detector ring assembly 30 includes the central opening 22, in which an object or patient, such as object 16 may be positioned, using, for example, the motorized table 24 (shown in FIG. 1). The motorized table 24 is aligned with the central axis of the detector ring assembly 30. During operation, the motorized table 24 moves the object 16 into the central opening 22 of the detector ring assembly 30 in response to one or more commands received from an operator workstation 34. More specifically, a PET scanner controller 36 responds to the commands received from an operator workstation 34 through a communication link 38. Therefore, the scanning operation is controlled from the operator workstation 34 through PET scanner controller 36.

The workstation 34 may be embodied as a personal computer (PC) that is positioned near the PET imaging system 14 and hard-wired to the PET scanner controller 36 via the communication link 38. The workstation 34 may also be embodied as a portable computer such as a laptop computer or a hand-held computer that transmits information to the PET scanner controller 36. In one embodiment, the communication link 38 may be hardwired between the PET scanner controller 36 and the workstation 34. Optionally, the communication link 38 may be a wireless communication link that enables information to be transmitted to or from the workstation to the PET scanner controller 36 wirelessly. In the exemplary embodiment, the workstation 34 controls real-time operation of the PET imaging system 14. The workstation 34 is also programmed to perform medical image diagnostic acquisition and reconstruction processes described herein.

The operator workstation 34 includes a central processing unit (CPU) or computer 40, a display 42 and an input device 44. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 40 executes a set of instructions that are stored in one or more storage elements or memories, in order to process input data. The storage elements may also store data or other information as desired or needed. The storage element may be in the form of an information source or a physical memory element within the computer 40.

The set of instructions may include various commands that instruct the computer or processor 40 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The CPU 40 connects to the communication link 38 and receives inputs, e.g., user commands, from the input device 44. The input device 44 may be, for example, a keyboard, mouse, a touch-screen panel, and/or a voice recognition system, etc. Through input device 44 and associated control panel switches, the operator can control the operation of the PET imaging system 14 and the positioning of the object 16 for a scan. Similarly, the operator can control the display of the resulting image on the display 42 and can perform image-enhancement functions using programs executed by the workstation CPU 40.

During operation of one exemplary detector, when a photon collides with a scintillator on the detector ring assembly 30, the photon collision produces a scintilla on the scintillator. The scintillator produces an analog signal that is transmitted on a communication link 46 when a scintillation event occurs. A set of acquisition circuits 48 is provided to receive these analog signals. The acquisition circuits 48 produce digital signals indicating the 3-dimensional (3D) location and total energy of each event. The acquisition circuits 48 also produce an event detection pulse, which indicates the time or moment the scintillation event occurred.

The digital signals are transmitted through a communication link, for example, a cable, to a data acquisition controller 52. The data acquisition controller 52 is adapted to perform the motion characterization and image reconstruction processes as described herein and various other functions. In one embodiment, the controller 52 is positioned remotely from the workstation 34 and communicates with the workstation 34 and PET scanner controller 36 via a communication link 54. Optionally, the controller 52 may be embedded within the workstation 34. For example, the controller 52 may be physically separate from the CPU 40 and used in conjunction with the CPU 40 to improve or enhance the image processing speed. In another embodiment, the CPU 40 may perform all the processing functions performed by the controller 52, e.g. the controller 52 is embedded in the workstation 34 such that CPU 40 performs the normalization and image reconstruction processes performed by the controller 52.

In one embodiment, the data acquisition controller 52 includes a data acquisition processor 60 and an image reconstruction processor 62 that are interconnected via a communication link 64. During operation, the acquisition circuits 48 transmit the digital signals to the data acquisition processor 60. The data acquisition processor 60 then performs various image enhancing techniques on the digital signals and transmits the enhanced or corrected digital signals to the image reconstruction processor 62 as discussed in more detail below.

In the exemplary embodiment, the data acquisition processor 60 includes at least an acquisition CPU or computer 70. The data acquisition processor 60 also includes an event locator circuit 72 and a coincidence detector 74. The acquisition CPU 70 controls communications on a back-plane bus 76 and on the communication link 64. During operation, the data acquisition processor 60 periodically samples the digital signals produced by the acquisition circuits 48. The digital signals produced by the acquisition circuits 48 are transmitted to the event locator circuit 72. The event locator circuit 72 processes the information to identify each valid event and provide a set of digital numbers or values indicative of the identified event. For example, this information indicates when the event took place and the position of the scintillator that detected the event. The events are also counted to form a record of the single channel events recorded by each detector element. An event data packet is communicated to the coincidence detector 74 through the back-plane bus 76.

The coincidence detector 74 receives the event data packets from the event locator circuit 72 and determines if any two of the detected events are in coincidence. Coincidence is determined by a number of factors. First, the time markers in each event data packet must be within a predetermined time period, for example, 12.5 nanoseconds, of each other. Second, the line-of-response (LOR) formed by a straight line joining the two detectors that detect the coincidence event should pass through the field of view in the PET imaging system 14. Events that cannot be paired are discarded. Coincident event pairs are located and recorded as a coincidence data packets by the coincidence detector 74 and are communicated through the back-plane bus 76 to a motion characterization module 78. The output from the coincidence detector 74 is referred to herein as an emission data set 80 or raw image data. In one embodiment, the emission data set 80 may be stored in a memory 82 that is located in the data acquisition processor 60. Optionally, the emission data set 80 may be stored in the workstation 34. As shown in FIG. 2, in the exemplary embodiment the output from the motion sensor 29 is also transmitted to the motion characterization module 78. The operation of the motion characterization module 78 is discussed in more detail below.

Figure 3:
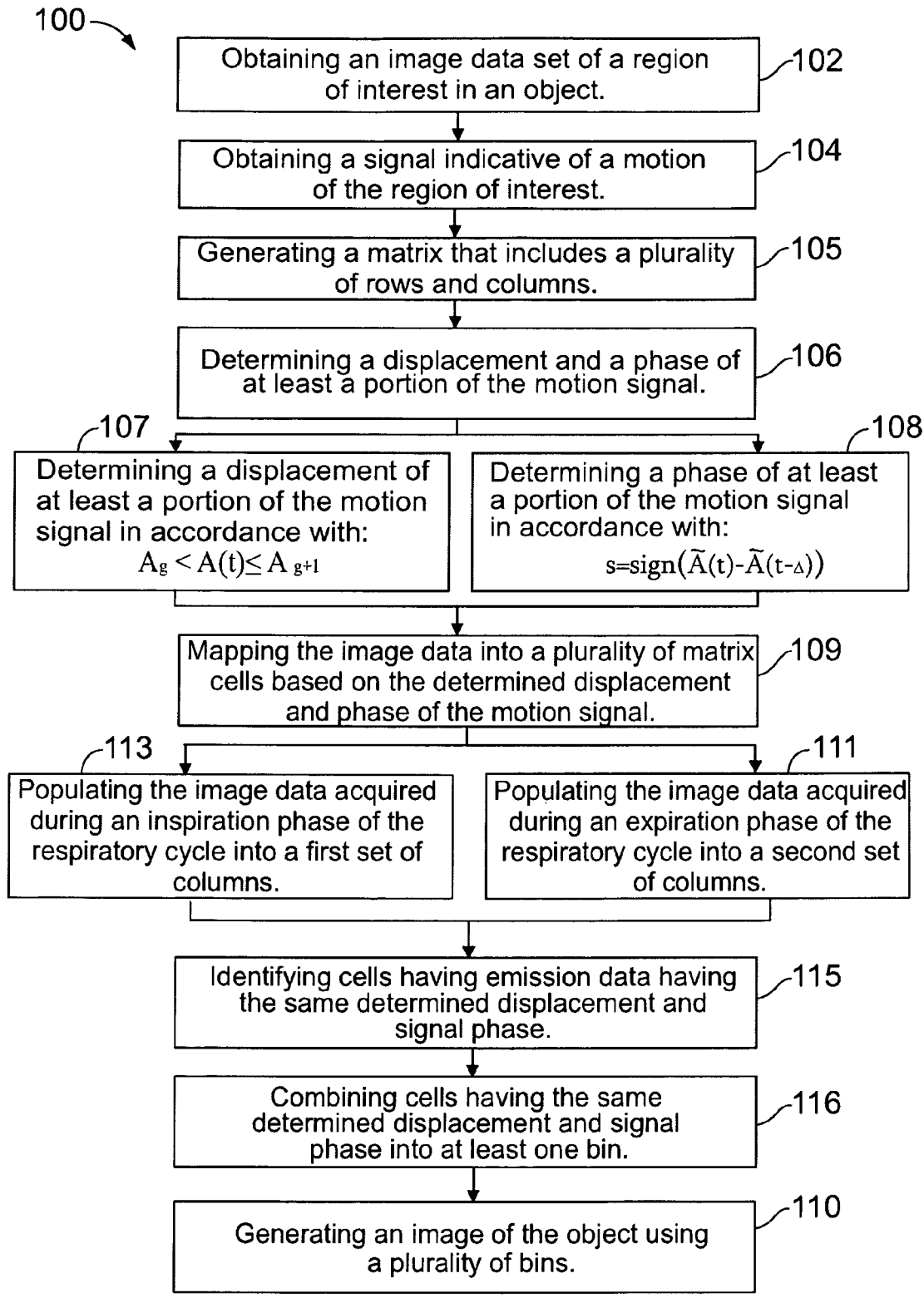
FIG. 3 is a flowchart illustrating an exemplary method for reducing artifacts in an image that result from motion of an object being imaged.

FIG. 3 is a simplified block diagram of an exemplary method performed by the PET imaging system 14 shown in FIG. 2 in accordance with an embodiment of the present invention. In the exemplary embodiment, the method 100 may be implemented using the motion characterization module 78. The method 100 performs motion characterization, or motion reduction, on the emission data set 80 to account for the motion of the object 16 based on the motion signal received from the motion sensor 29 shown in FIG. 1. More specifically, the method 100 identifies the motion of the object 16 and re-organizes the emission data set 80 to enable a motion-reduced image of the object 16 to be reconstructed. It should be realized that although method 100 is described with respect to the emission data set 80 obtained from the PET imaging system 14, that method 100 may be applied to a transmission data set obtained from the CT imaging system 12. Moreover, the method 100 may be applied to any image data obtained using any of the imaging modalities discussed herein, and that the emission data set 80 is exemplary only.

At 102, an image data set of a region of interest 17 of the object 16 (each shown in FIG. 1) is obtained. In the exemplary embodiment, the emission data set 80 is obtained using the second modality 14 (shown in FIG. 2). For example, the second modality 14 may be a PET imaging system producing a PET emission data set or a SPECT imaging system producing a SPECT emission data set. The emission data set 80 may be obtained by performing an emission scan of the object 16 to produce the emission data set 80. Optionally, the emission data set 80 may be obtained from data collected during a previous scan of the object 16, wherein the emission data set 80 has been stored in a memory, such as memory device 82

(shown in FIG. 2). The emission data set 80 may be stored in any format, such as a list mode data set for example. Moreover, the emission data set 80 and an attenuation data set may be obtained from a remote memory such as the memory installed in workstation 34 (shown in FIG. 2). The emission data set 80 and the attenuation data set may be obtained during real-time. For example, the methods described herein may be performed on emission data as the emission data is received from the acquisition circuits 48 during a real-time examination of the object 16. In the exemplary embodiment, the emission data set 80 includes the data representative of emission particles emitting from a region of interest 17 of object 16.

Figure 4:
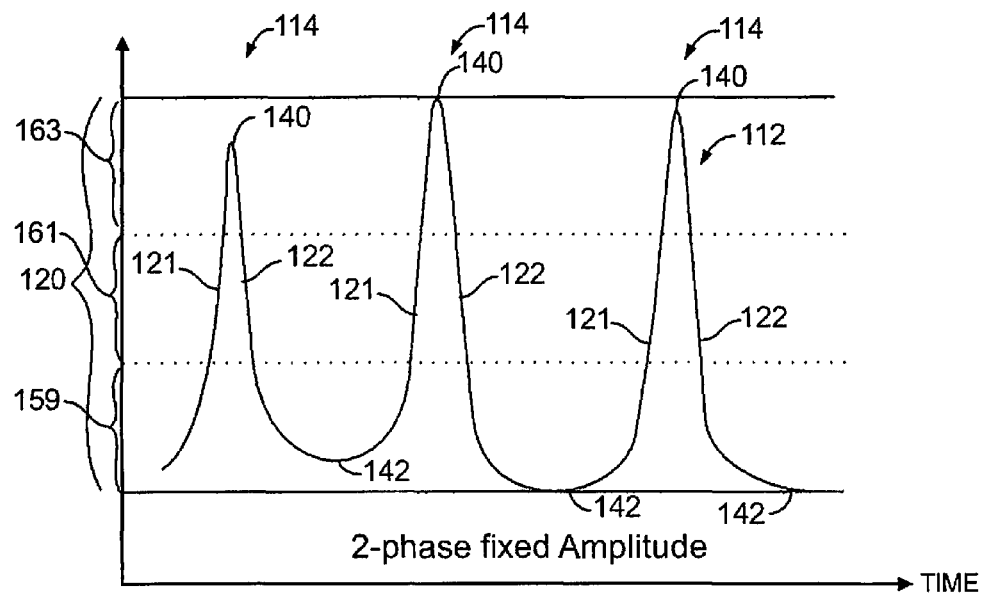
FIG. 4 is an exemplary motion signal generated using the system illustrated in FIG. 1 in accordance with an embodiment of the present invention.

At 104 a signal indicative of motion of the region of interest 17 of object 16 is obtained. For example, FIG. 4 illustrates an exemplary motion signal 112 that is obtained at the operation 104. The motion signal 112 may be obtained during a PET imaging scan, during a CT imaging scan, or during any other medical imaging system scanning procedure. Optionally, the motion signal 112 may be obtained from a database of previous medical examination procedures. As shown in FIG. 4, the Y-axis represents a displacement of the motion signal 112 and the X-axis represents time. In the exemplary embodiment, the motion signal 112 is obtained using the motion sensor 29 shown in FIG. 1. Optionally, the motion signal 112 may be obtained from information saved in a memory device, such as memory 82. In the exemplary embodiment, the motion signal 112 is representative of the motion of object 16. The motion signal 112 includes a plurality of cycles 114 wherein each cycle includes a phase 121 that is increasing, a phase 122 that is decreasing, a maximum displacement value 140, and a minimum displacement value 142. The figure also indicates the range 120 of displacement values. Optionally, imaging system 10 may use a device that injects a trigger signal into the PET and/or CT data stream. In the exemplary embodiment, the motion characterization module 78 is adapted to obtain or receive the motion signal from the motion sensor 29.

Referring again to FIG. 3, at 105 the motion characterization module 78 generates a matrix that includes a plurality of rows 132 and columns 134. For example, at operation 105, the motion characterization module 78 generates the exemplary matrix 130 shown in FIG. 5. The motion characterization module 78 is adapted to receive the emission data set 80 and utilize a motion signal, such as the exemplary motion signal 112, to bin the emission data set 80 into the matrix 130 as is discussed in more detail below. The matrix 130 includes a plurality of rows 132 and columns 134. The rows 132 and columns 134 define a plurality of bins or cells 136. In the exemplary embodiment, the matrix 130 includes three rows 132 and six columns 134 resulting in a matrix that includes eighteen cells 136. It should be realized that matrix 130 is exemplary, and that during operation, matrix 130 typically includes a sufficient quantity of rows 132 and columns 134 to enable emission data collected over an entire PET imaging procedure to be analyzed.

Referring again to FIG. 3, at 106 the displacement 161 and the phase 122 of at least a portion of the motion signal 112 shown in FIG. 4 is determined using a motion signal analysis module 84, shown in FIG. 2, for example. During operation, the motion signal 112 is used for dual gating the emission data. For example, referring again to FIG. 5, each cycle 114 of the motion signal 112 is divided into time intervals or phases based on the detected changes in the cycle 114 using the motion signal analysis module 84. In the exemplary embodiment, the motion signal 112 is used for both displacement gating and phase gating, e.g. to determine if the patient is in the inspiration stage, e.g. phase 121, or the expiration stage, e.g. phase 122. In one embodiment, a device may generate a trigger at a particular point in the breathing cycle. The phase can be determined using the percent time between two triggers. In another embodiment, the phase or direction of the breathing can be inferred by looking at the history of the motion signal 112 and calculating the difference of the current motion signal 112 and the value of the motion signal that was acquired approximately 200 ms earlier, for example. To reduce noise, this difference may also be determined on a denoised version of the motion signal 112 (e.g. moving average). This difference can then be used as indicator of the phase of the breathing, e.g. whether the breathing is inspiration or expiration. The phase and displacement of the motion signal 112 are used to identify and bin the emission data set 80 as is discussed in more detail below.

Referring again to FIG. 3, at operation 107, the (discretized) displacement value g of the motion signal 112 is determined in accordance with:

$$A_g(t) < A(t) < A_{g+1}(t) \quad \text{(Eqn. 1)}$$

where $A_g(t)$ and $A_{g+1}(t)$ define the displacement boundaries of each cell 136 to which the emission data is assigned based on the displacement of the motion signal 112; and A(t) is the motion signal 112 over time. The displacement boundaries defined by $A_g$ may vary with respect to time. For example, the displacement boundaries may vary among multiple cycles 114.

At operation 108, the phase, e.g. phase 121 and/or phase 122 of the motion signal 112 is determined. More specifically, the phase or direction of the motion signal 112, e.g. increasing or decreasing, inspiration or expiration is determined in accordance with:

$$s = \text{sign}(\tilde{A}(t) - \tilde{A}(t-\Delta)) \quad \text{(Eqn. 2)}$$

where s denotes the direction of the motion signal 112; ($\tilde{A}(t)$) denotes the (optionally processed) motion signal 112 at a given time; and $\Delta$ denotes a time constant that is preselected based on the expected hysteresis; for example $\Delta \cong 200$ milliseconds. In one embodiment, A may be smaller than an expected period of the phase of the motion signal 112. $\Delta$ may be significantly smaller than the phase period, but not so small that $\Delta$ would be sensitive to noise. By way of example only, $\Delta$ may be less than one tenth of the phase period of the motion signal 112. In one embodiment, the motion signal is processed using a denoising filter. For example, ($\tilde{A}(t)$) would be computed by a running average of the original signal (A(t)). While only two phases 121, 122 are referred to in the example above and shown in FIG. 4, a different number of phases may be determined. For example, three or more phases may be determined at 108. As an example of using more phases, 2 "resting" phases could be added to the Inspiration (I) and Expiration (E) phases, one at end-of-inspiration (EI) and one at end-of-expiration (EE) as follows:

$$d = (\tilde{A}(t) - \tilde{A}(t-\Delta))$$

if $d < T_1(t)$, then s=I, else if $d < T_2(t)$ then s=E, else if the previous phase s was I, then s=EI, else s=EE.

where $T_1$ and $T_2$ are (potentially time-dependent) thresholds.

Figure 5:
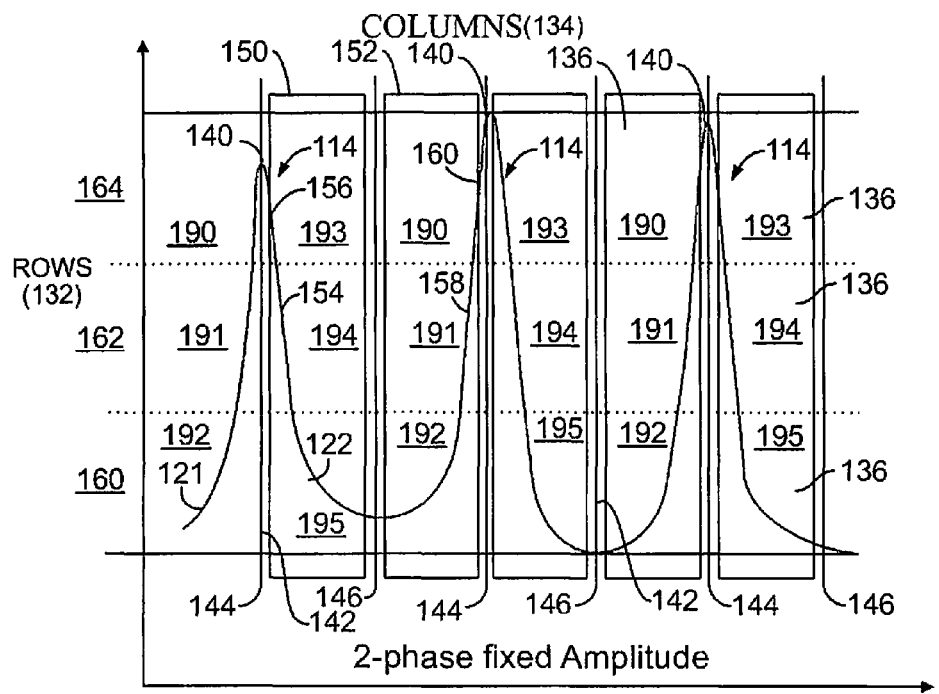
FIG. 5 is an exemplary matrix that may be generated using the exemplary method shown in FIG. 3 in accordance with an embodiment of the present invention.

As shown in FIG. 5, the Y-axis represents the rows 132 of the matrix 130 and the Y-axis represents the columns of the matrix 130. The rows 132 and columns 134 are arranged based on the displacement of the motion signal 112 and the columns 134 are arranged based on the phases 121 and 122 of the motion signal.

At 109 the emission data set 80 is mapped into the matrix 130 based on the determined discretized displacement g and phases of the signal 112 using a matrix populating or building module 85 shown in FIG. 2. The matrix populating module 85 populates the matrix 130 based on both the displacement and phase of portions of the motion signal 112. The matrix populating module 85 may be embodied as a set of instructions or an algorithm. For example, the matrix populating module 85 may be a mathematical algorithm or a logical representation of the processes utilized to determine the cell 136 in which the emission data is to be assigned.

For example, referring again to FIG. 5, as discussed above, the motion signal analysis module 84 may perform phase gating by determining local minima and maxima of the motion signal 112. By way of example only, the motion signal analysis module 84 may determine the maximum 140 and minimum 142 displacement values for each respiratory cycle 114. The maximum displacement values 140 are represented for each cycle 114 by a line 144 and the minimum displacement values 142 are represented for each cycle 114 by a line 146. The maximum and minimum displacement values 140 and 142 are used to define the boundaries, e.g. the lines 144 and 146, of each column 134. Alternatively, the boundaries of each column 134 may be defined using Equation 2 or any of the other phase gating methods described above.

Referring again to FIG. 3, at 111, the matrix populating module 85 then populates the matrix 130 with emission data 80 based on the information received from the motion signal analysis module 84, e.g. the phase and displacement for each cycle 114 in the motion signal 112. For example, referring again to FIG. 5, the matrix populating module 85 populates the image data 80 acquired during an inspiration phase of a first respiratory cycle into a first column 150. The matrix populating module 85 then populates the matrix 130 with emission data 80 acquired during an inspiration phase of a second respiratory cycle into a second column 152. As shown in FIG. 5, the column 152 includes the emission data that was collected during an inspiration phase 158 of a breathing cycle 160 following the expiration phase data stored in column 150. This procedure is repeated for emission data collected throughout a plurality of breathing cycles 114, wherein each breathing cycle 114 includes an inspiration phase and an expiration phase. In the exemplary embodiment, columns including inspiration information are interleaved with columns including expiration information.

Referring back to FIG. 3, at 113 the matrix populating module 85 populates the matrix 130 with emission data 80 based on the maximum displacement value 140 of each cycle 114. Accordingly, the matrix populating module 85 populates the matrix 130 with emission data 80 based on the both the displacement value and phase of the motion signal 112. For example, referring again to FIG. 5, the columns 134 are populated based on the phase values of the motion signal 112, and the rows 132 are populated based on the displacement values of the motion signal 112. In the exemplary embodiment, the matrix is subdivided into a plurality of cells in accordance with: Cells=M×N, where M is a quantity of columns 134 and N is a quantity of rows 132. It should be realized that the quantity of columns 134 and rows 132 is exemplary only, and that the matrix 130 may include more or fewer than three rows 132 and six columns 134. In the exemplary embodiment, the quantity of columns 134 and rows 132 are based on the range of the displacement of the motion signal 112 and the phase of the motion signal 112, e.g. inspiration or expiration.

In the exemplary embodiment, the motion signal 112 includes three cycles 114, wherein each cycle 114 has an inspiration and expiration phase. Accordingly, in the exemplary embodiment, the matrix 130 includes six columns 134, wherein each column is adapted to receive emission data related to a specific phase, either inspiration or expiration, of a single cycle 114. For example, the first column 150 includes the emission data that was collected during an expiration phase 154 of a first exemplary breathing cycle 156 and the second column includes the emission data 80 acquired during an inspiration phase of the respiratory cycle.

Additionally, the quantity of rows 132 is based on a quantity of ranges that the displacement of the motion signal 112 is divided. More specifically, the motion signal 112 may be divided into any quantity of ranges based on the displacement of the motion signal. In the exemplary embodiment, the displacement of the motion signal 112 is divided into three displacement ranges 159, 161, and 163, for example. Referring to FIG. 5, a first row 160 includes the emission data that having displacement value defined in the range between 0 and 1, a second row 162 includes the emission data having a displacement value defined in the range between greater than 1 and less than 2, and a third row includes the emission data having a displacement value defined in the range between greater than 2 and 3. It should be realized that the ranges used to define the rows 132 are exemplary only, and that the ranges may be selected based on the expected displacement values of the motion signal 112. As discussed above, each cell 136 in the matrix 130 includes emission data that is defined based on the displacement of the motion signal 112 and the phase of the motion signal 112.

Figure 6:
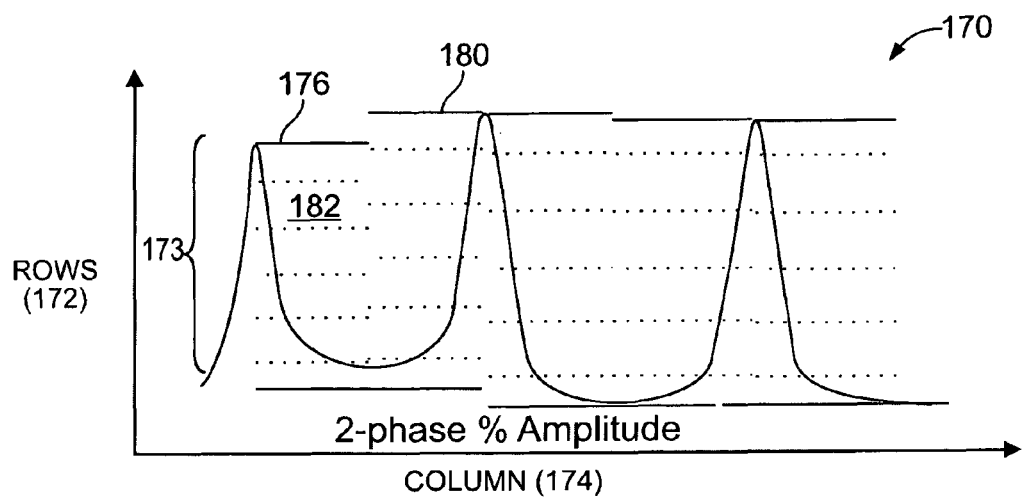
FIG. 6 is another exemplary matrix that may be generated using the exemplary method shown in FIG. 3 in accordance with an embodiment of the present invention.

FIG. 6 is another exemplary matrix 170 that may be generated using the exemplary method shown in FIG. 3. As shown in FIG. 6, the rows 132 are defined based on a fixed range of displacement values as discussed above. The matrix 170 is divided into a plurality of rows 172 and columns 174 as discussed above with respect to FIG. 5. In this exemplary embodiment, each column 174 may be subdivided into a plurality of rows 172, wherein at least some of the rows 172 have a variable displacement value. For example, a first column 176, e.g. the expiration phase, is subdivided into a plurality of rows 178 based on a first range of displacement values, whereas a second column 180, e.g. the inspiration phase, is subdivided into a plurality of rows 182 based on a second range of displacement values that is different than the first range. In the exemplary embodiment, the displacement boundaries defining the rows 178 are changed or varied for every half-breathing cycle. Utilizing variable displacement values with respect to the inspiration and expiration phases facilitates further compensating for the effects of hysteresis on the emission data.

The matrix populating module 85 utilizes the displacement values and phases determined by the motion signal analysis module 84 to populate both the matrix 130 and matrix 170 with emission data 80. For example, the matrix populating module 85 utilizes mathematical language to gate the emission data located at a predetermined time to a cell (g, s) based on both the displacement and phase of the motion signal 112 at the given time. The cell (g, s) and the cycle number are each used to construct the matrix.

Referring again to FIG. 3, at 115, the cells 136 including emission data having the same determined displacement and signal phase are identified. Referring again to FIG. 5, cells 136 having emission data associated with the same phase and the same displacement value are identified using the motion characterization module 74. In the exemplary embodiment, the matrix 130 includes six different cells 190-195 that each includes emission data having the same phase and the same range of displacement values. For example, each cell 190 includes emission data associated with the same phase and the same range of displacement values. Moreover, each cell 192 includes emission data associated with the same phase and the same range of displacement values, etc. through cell 195.

Figure 7:
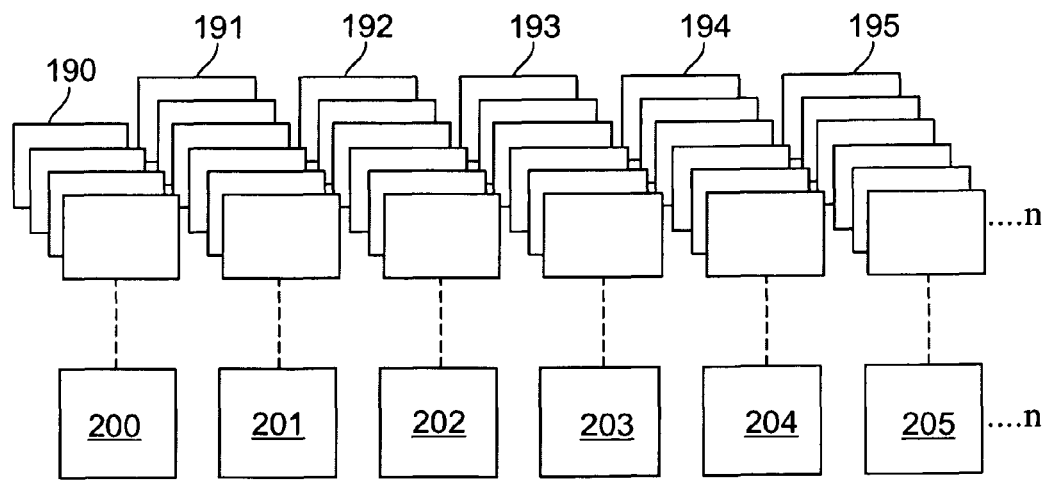
FIG. 7 is a block diagram illustrating a portion of the method shown in Figure in accordance with an embodiment of the present invention.

After the cells are identified at operation 115, the cells including emission data are combined at 116 into at least one bin. In one embodiment, cells having the same phase and the same range of displacement values are identified and combined into a single bin. For example, FIG. 7 illustrates the cells 190-195 shown in FIG. 6 and a respective bin 200-205 adapted to receive the information from a respective cell 190-195. It should be realized that the quantity of bins illustrated in FIG. 7 is exemplary, and that during operation, fewer or a greater quantity of bins may be used based on the matrix as discussed above. As such, each bin 200-205, respectively includes emission data associated a plurality of cycles 114. More specifically, each bin 200-205 is adapted to receive emission data acquired over a plurality of cycles, wherein each cycle has the same phase and the same range of displacement values. Accordingly, each bin 200-205 includes emission data representing a certain motion state of the object 16. In other words, when an organ having a more or less periodical motion is imaged, the emission data is rearranged such that projections acquired at a similar phase or motion state and a similar displacement are binned into the same temporal bin, e.g. bins 200-205.

For example, referring again to FIG. 5, the matrix includes six cells each identified by number 190. Each cell numbered 190 includes emission data having the same phase and the same range of displacement values. During operation, each cell numbered 190 is combined into a common bin, e.g. bin 200. Accordingly, bin 200 includes emission data having the same phase and the same range of displacement values obtained over a plurality of cycles 114. The above described method is used to generate the remaining bins 201-205 from the initial cells 13 6 contained in the matrix 130.

In another embodiment, the decision as to which bin 200-205 an event belongs may be made on the basis of information acquired using the respiratory sensor 60 or on another motion signal. For example, if it is determined that motion is substantially periodic, the number of bins may be reduced, e.g. the displacement range could even be ignored when combining cells. As another example, at least some of the matrix cells may be designated "abnormal" and therefore rejected or combined into a "low-resolution" bin. For example, a cycle could be designated as irregular, and cells during this cycle as "abnormal". As another example, this designation could be made on the basis of the displacement and phase range of the cell. This relies on the fact that data acquired during "regular" cycles will fill only part of the matrix. Examples of "abnormal" data in the case of respiratory movement include very deep breaths which will have larger displacements than average (during part of the cycle); and very shallow breaths which will have smaller displacements than average (usually during inspiration and expiration, but not during the resting phase at the end of expiration, so it might be advantageous to use more than 2 phase ranges for this example). Abnormality of a displacement and phase range could be determined on the basis of its duration, i.e. the amount of time during which the motion signal occurred in the corresponding cells. For example, if the duration of a particular displacement and phase range is substantially lower than for other ranges, the information in the corresponding matrix cells may be designated "abnormal" , and hence rejected or combined into a "low-resolution" bin. Optionally, abnormality may also be decided from a training set of curves (e.g. acquired with the motion tracker before acquisition) or from another (supposedly matching) data-set. Data from two subsequent acquisitions which have been classified as belonging to cells in the matrix corresponding to the same displacement and phase range can have matching locations of the organs. Therefore, cells corresponding to a displacement and phase range for which no signal occurred during one of the acquisitions could be rejected (or combined). One example includes matching CT and PET data. From the above examples, it should be clear that cells belonging to different displacement and phase ranges can potentially be combined into the same bin. In another exemplary embodiment, A method the cells having a different pre-determined displacement ranges and pre-determined signal phase ranges may be combined into a single low-resolution bin based on a second motion signal.

Referring again to FIG. 3, at 110 an image of the object is generated using the matrix 130. In the exemplary embodiment, generating 110 an image of the object using the matrix includes reconstructing an image of the object 16 using the bins 200-$n$. In the exemplary embodiments described above, the image is reconstructed using a sorter/histogrammer shown in FIG. 2.

Referring again to FIG. 2, the motion characterized emission data set is then transmitted to the sorter/histogrammer 210 to generate a data structure known as a histogram. A histogram includes a large number of bins, where each bin corresponds to one or more unique pairs of detector scintillators in the PET scanner and motion state as determined by the motion characterization module 78. The histogrammer 210 may also take other information into account such as detected energies and/or arrival times, e.g. in a Time of Flight PET scanner and/or for dynamic data. Because a PET scanner typically includes thousands of detector scintillators, the histogram typically includes millions of bins. Each bin of the histogram also stores a count value representing the number of coincidence events detected by the pair of detector scintillators for that bin during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 62 also includes a memory module 212, an image CPU 214, an array processor 216, and a communication bus 218. During operation, the sorter/histogrammer 210 counts all events in the bins of the histogram as discussed above. This data is organized in one exemplary embodiment as a data array 220. The data array 220 is stored in the memory module 212. The communication bus 218 is linked to the communication link 76 through the image CPU 214. The image CPU 214 controls communication through communication bus 218. The array processor 216 is also connected to the communication bus 218. The array processor 216 receives the data array 220 as an input and reconstructs images in the form of image arrays 222. Resulting image arrays 222 are then stored in memory module 212. The images stored in the image array 222 are communicated by the image CPU 214 to the operator workstation 34.

A technical effect of method 100 is to provide a fully automatic method of characterizing and reducing imaging artifacts caused by hysteresis in either transmission or emission data. Specifically, a matrix of cells is generated. Each cell in the matrix includes emission data having both a displacement value and a phase value. Similar cells, e.g. cells having both a common phase value, and falling within a common range of displacement values, may then be combined into a single bin. The bins may then be used to generate an image of the object. Moreover, since each bin includes similar displacement and phase values, the effects of hysteresis is either reduced and/or eliminated. As a result, the image(s) generated using the bins has(have) less artifacts than known imaging methods.

Moreover, the method and apparatus described herein combine the features of both displacement and phase-based gating to keep the advantages of displacement-based gating, but take some of the hysteresis effect into account. The method describes the use of two or more sets of gates, e.g. one set of gates for inspiration and one set of gates for expiration. During completely regular breathing, the method described herein includes the same advantages as phase-based gating and also works well for very elastic tissue. During irregular breathing, the method described herein takes the displacement of the breathing into account. In particular, the method described herein results in better motion-freezing than either displacement or phase-based gating. The method described herein is useful during medical imaging, and in other cases where the location of the internal structures need to be known, and in particular for radiotherapy. The method described herein may also be used outside of medical imaging wherein the motion is mainly correlated by the displacement of a certain signal, but some hysteresis is observed.

The methods and apparatus described herein provide a fully automatic method of characterizing and reducing imaging artifacts caused by hysteresis in either transmission or emission data. A technical effect of the above describes methods is to increase the accuracy of identifying the location of lesions and other features desired to be observed by the operator.

Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for reducing, in an image, motion related imaging artifacts, said method comprising:
   obtaining imaging data of an object using an imaging system;
   obtaining a motion signal indicative of motion in the object from the imaging system;
   determining a displacement and a phase of at least a portion of the motion signal using a computer;
   generating a matrix that includes at least one inspiration phase column and at least one expiration phase column using the computer;
   subdividing the inspiration phase column and the expiration phase column into a plurality of cells, each cell configured to store imaging data within a different displacement range;
   mapping the imaging data into the plurality of cells based on the displacement and phase of the imaging data; and
   generating, using the computer, an image of the object using the data within at least one of the cells.

2. A method in accordance with claim 1, wherein the obtaining the imaging data further comprises obtaining at least one of a PET emission and a SPECT emission imaging data.

3. A method in accordance with claim 1, wherein the matrix includes a plurality of rows, said method further comprises:
   combining the cells having the same displacement range and phase into a single bin.

4. A method in accordance with claim 1, wherein the determining operation further comprises determining the displacement of the motion signal in accordance with:

$$A_g(t) < A(t) \leq A_{g+1}(t)$$

where $A_g(t)$ and $A_{g+1}(t)$ define the displacement ranges of each cell to which the imaging data is mapped based on the displacement of the motion signal; and $A(t)$ is the motion signal over time.

5. A method in accordance with claim 4, wherein the determining operation further comprises determining the phase of the motion signal in accordance with:

$$s=\text{sign}(\tilde{A}(t)-\tilde{A}(t-\Delta))$$

where s denotes the direction of the motion signal; ($\tilde{A}(t)$) denotes a denoised displacement of the motion signal at a predetermined time; and Δ denotes a time constant that is preselected based on an expected hysteresis.

6. A method in accordance with claim 1, wherein the matrix includes a plurality of rows, said method further comprises combining the cells having the same displacement range and the same phase into a single low-resolution bin.

7. A multi-modality imaging system comprising a first modality unit, a second modality unit, and a computer operationally coupled to the first and second modality units, wherein the computer is programmed to:
    obtain imaging data of an object;
    obtain a motion signal indicative of motion in the object;
    determine a displacement and a phase of at least a portion of the motion signal;
    generate a matrix that includes at least one inspiration phase column and at least one expiration phase column using the computer;
    subdivide the inspiration phase column and the expiration phase column into a plurality of cells, each cell including image data within a different displacement range;
    map the imaging data into the plurality of cells based on the displacement and phase of the imaging data; and
    generate an image of the object using the imaging data within at least one of the cells.

8. A multi-modality imaging system in accordance with claim 7, wherein the first modality comprises a computed tomography imaging system and the second modality comprises at least one of a Positron Emission Tomography system and a SPECT Imaging system.

9. A multi-modality imaging system in accordance with claim 7, wherein the computer is further programmed to:
    combine the cells having the same displacement range and the same phase into a single bin.

10. A multi-modality imaging system in accordance with claim 9, wherein the computer is further programmed to:
    identify the plurality of cells having data having the same displacement range and phase; and
    combine the cells having the same displacement range and phase into a single bin; and
    generate the image of the object using the single bin.

11. A multi-modality imaging system in accordance with claim 7, wherein the computer is further programmed to:
    determine the displacement of the motion signal in accordance with $$A_g(t)<A(t)\leq A_{g+1}(t)$$

where $A_g(t)$ and $A_{g+1}(t)$ define the displacement ranges of each cell to which the data is assigned based on the displacement of the motion signal; and A(t) is the motion signal over time; and
    determine a phase of the motion signal in accordance with $$s=\text{sign}(\tilde{A}(t)-\tilde{A}(t-\Delta))$$

where s denotes the direction of the motion signal; ($\tilde{A}(t)$) denotes a denoised displacement of the motion signal at a predetermined time; and Δ denotes a time constant that is preselected based on an expected hysteresis.

12. A non-transitory computer readable medium encoded with a program programmed to instruct a computer to:
    obtain imaging data an object;
    obtain a motion signal indicative of motion of object;
    determine a displacement and a phase of at least a portion of the motion signal;
    generate a matrix that includes at least one inspiratinspiration phase column and at least one expiration phase column;
    subdivide the inspiration phase column and the expiration phase cow m into a plurality of cells, each cell storing image data within a different displacement range;
    map the imaging data into the plurality of cells based on the displacement and phase of the imaging data; and
    generate an image of the object using the imaging data within at least one of the cells.

13. A non-transitory computer readable medium in accordance with claim 12 wherein the program is programmed to further instruct the computer to:
    identify the plurality of cells having data having the same displacement range and phase; and
    combine the cells having the same displacement range and phase into a single bin; and
    generate the image of the object using the single bin.

* * * * *

UNITED STATES PATENT AND TRADEMARK OFFICE
CERTIFICATE OF CORRECTION

PATENT NO. : 8,532,357 B2
APPLICATION NO. : 12/358829
DATED : September 10, 2013
INVENTOR(S) : Scott David Wollenweber and Kris Filip Johan Jules Thielemans Page 1 of 1

It is certified that error appears in the above-identified patent and that said Letters Patent is hereby corrected as shown below:

Title page, in item (73) Assignee: Add a second Assignee -- Hammersmith Imanet, Ltd., London, United Kingdom SW 15 5HX --.

Signed and Sealed this
Twenty-third Day of June, 2015

Michelle K. Lee
*Director of the United States Patent and Trademark Office*